(12) United States Patent
Mehta

(10) Patent No.: US 9,402,948 B2
(45) Date of Patent: Aug. 2, 2016

(54) NASAL RINSE TIP

(71) Applicant: Ketan C. Mehta, Santa Rosa, CA (US)

(72) Inventor: Ketan C. Mehta, Santa Rosa, CA (US)

(*) Notice: Subject to any disclaimer, the term of this patent is extended or adjusted under 35 U.S.C. 154(b) by 0 days.

(21) Appl. No.: 14/796,854

(22) Filed: Jul. 10, 2015

(65) Prior Publication Data

US 2015/0314061 A1 Nov. 5, 2015

Related U.S. Application Data

(63) Continuation of application No. 14/047,796, filed on Oct. 7, 2013, now Pat. No. 9,095,645, which is a continuation of application No. 13/458,921, filed on Apr. 27, 2012, now Pat. No. 8,562,556.

(60) Provisional application No. 61/480,361, filed on Apr. 28, 2011.

(51) Int. Cl.
| | |
|---|---|
| *A61M 3/02* | (2006.01) |
| *A61H 35/04* | (2006.01) |
| *B65D 83/20* | (2006.01) |
| *B65D 83/30* | (2006.01) |
| *B65D 83/62* | (2006.01) |
| *A61M 15/08* | (2006.01) |

(52) U.S. Cl.
CPC ............ *A61M 3/0262* (2013.01); *A61H 35/04* (2013.01); *A61M 3/0216* (2014.02); *A61M 3/0233* (2013.01); *A61M 3/0279* (2013.01); *B65D 83/20* (2013.01); *B65D 83/30* (2013.01); *A61H 2201/0153* (2013.01); *A61H 2201/0157* (2013.01); *A61H 2205/023* (2013.01); *A61M 15/08* (2013.01); *A61M 2202/04* (2013.01); *A61M 2205/3355* (2013.01); *A61M 2210/0618* (2013.01); *B65D 83/62* (2013.01)

(58) Field of Classification Search
CPC .............. A61M 15/08; A61M 1/0058; A61M 2210/0618; A61M 11/00; A61M 2205/3355
USPC .................. 128/200.14, 203.22; 604/30, 275; 606/162
See application file for complete search history.

(56) References Cited

U.S. PATENT DOCUMENTS

| | | |
|---|---|---|
| 2,135,052 A | 11/1938 | Rose |
| 3,186,645 A | 6/1965 | Eberlein |
| 3,471,092 A | 10/1969 | Hickey |
| 4,650,094 A | 3/1987 | Werding |

(Continued)

FOREIGN PATENT DOCUMENTS

| | | |
|---|---|---|
| FR | 2 387 047 | 11/1978 |
| JP | 2005-287669 A | 10/2005 |

(Continued)

OTHER PUBLICATIONS

Authorized Officer Ji Myong Nho, International Search Report and Written Opinion in PCT/US2010/050434, mailed Jun. 21, 2011, 9 pages.

(Continued)

*Primary Examiner* — Gerald Landry, II
(74) *Attorney, Agent, or Firm* — Fish & Richardson P.C.

(57) ABSTRACT

A device for nasal lavage is described. The device ejects a gentle flow of fluid under pressure. The fluid stream provides a high quantity of fluid at low pressure. The low pressure fluid stream is more comfortable for a user than a high pressure fluid stream that are delivered by various types of pressurized cans of solution.

17 Claims, 14 Drawing Sheets

(56) References Cited

U.S. PATENT DOCUMENTS

| | | | |
|---|---|---|---|
| 5,116,311 | A | 5/1992 | Löfstedt |
| 5,806,723 | A | 9/1998 | DuBose |
| 5,906,198 | A | 5/1999 | Flickinger |
| 6,520,384 | B2 | 2/2003 | Mehta |
| 6,644,305 | B2 * | 11/2003 | MacRae ............ A61M 15/0086 128/200.14 |
| 7,302,948 | B2 | 12/2007 | Anderson |
| 2002/0158089 | A1 | 10/2002 | Mehta |
| 2004/0068222 | A1 | 4/2004 | Brian |
| 2004/0116892 | A1 * | 6/2004 | Burroughs ............ A61J 1/2096 604/414 |
| 2005/0098172 | A1 * | 5/2005 | Anderson ........... B05B 11/3091 128/200.23 |
| 2005/0210572 | A1 | 9/2005 | Fogel |
| 2007/0060868 | A1 * | 3/2007 | Tsutsui ............. A61M 15/0028 604/58 |
| 2008/0008979 | A1 | 1/2008 | Thomas et al. |
| 2008/0154183 | A1 | 6/2008 | Baker et al. |
| 2008/0312674 | A1 | 12/2008 | Chen et al. |
| 2009/0281454 | A1 * | 11/2009 | Baker ................. A61M 1/0058 600/573 |
| 2010/0012680 | A1 * | 1/2010 | Canfield ................ A45D 34/04 222/207 |
| 2011/0077603 | A1 * | 3/2011 | Mehta ................... A61M 3/025 604/246 |
| 2011/0144588 | A1 * | 6/2011 | Taylor ................. A61M 3/0258 604/151 |
| 2011/0155750 | A1 | 6/2011 | Bernstein et al. |
| 2012/0277675 | A1 | 11/2012 | Mehta |
| 2013/0197450 | A1 | 8/2013 | Mehta |
| 2014/0039411 | A1 | 2/2014 | Mehta |
| 2015/0005714 | A1 | 1/2015 | Mehta |

FOREIGN PATENT DOCUMENTS

| | | | |
|---|---|---|---|
| KR | 10-2000-0066190 A | | 11/2000 |
| WO | WO 02/07668 A1 | | 1/2002 |

OTHER PUBLICATIONS

Authorized officer Agnès Wittmann-Regis, International Preliminary Report on Patentability in PCT/US2010/050434, mailed Apr. 5, 2012, 6 pages.

Authorized officer Cheol Soo Lee, International Search Report and Written Opinion in PCT/US2012/035616, mailed Nov. 26, 2012, 9 pages.

Authorized officer Philippe Bécamel, International Preliminary Report on Patentability in PCT/US2012/035616, mailed Nov. 7, 2013, 6 pages.

OCEAN Complete® [online]. Fleming Pharmaceuticals, 2009 [retrieved on Dec. 29, 2009]. Retrieved from the Internet: <URL: http://flemingpharma.com/content/view/141/140/, 2 pages.

OCEAN Ultra® Sterile Saline Nasal Mist [online]. Fleming Pharmaceuticals, 2009 [retrieved on Dec. 29, 2009]. Retrieved from the Internet: <URL: http://flemingpharma.com/content/view/84/81/, 1 page.

SinuCleanse Squeeze™ [online]. Med-Systems, Inc., 2008 [retrieved on Dec. 29, 2009]. Retrieved from the Internet: <URL: http://www.sinucleanse.com/product/squeeze.htm, 3 pages.

Supplementary European Search Report in Application No. EP 12 77 7087, mailed May 12, 2015, 8 pages.

* cited by examiner

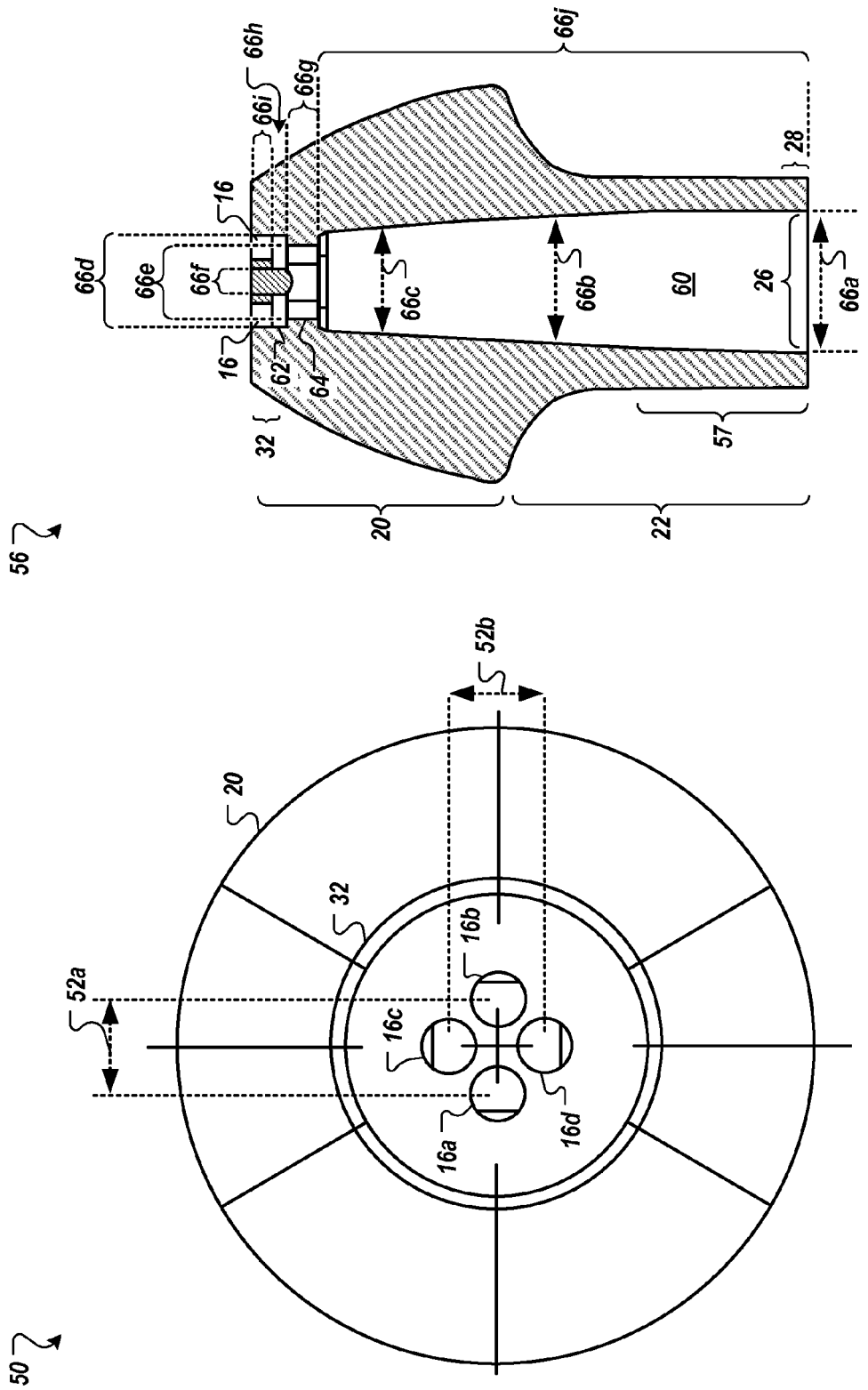

NASAL RINSE TIP

CROSS-REFERENCE TO RELATED APPLICATIONS

This is a continuation U.S. application Ser. No. 14/047,796, filed Oct. 7, 2013, which is a continuation of U.S. application Ser. No. 13/458,921, filed Apr. 27, 2012 (now U.S. Pat. No. 8,562,556), which claims the benefit of U.S. Provisional Application No. 61/480,361, filed Apr. 28, 2011. Both of these applications are incorporated by reference herein in their entirety.

FIELD

This disclosure relates to lavage.

BACKGROUND

People in many parts of the world perform nasal cleansing (or nasal irrigation) using a neti pot or other product on a routine basis, like brushing their teeth or showering. Nasal cleansing is even incorporated into some forms of yoga practice, such as in Jala neti. Jala neti is a Sanskrit term that refers to cleansing and translates to "water cleansing". The solution for rinsing the nasal passages using a neti pot or other product can be a saline solution. Some people use nasal rinsing to reduce allergies, improve breathing, eliminate post-nasal drip or sinus infections, moisten dry nasal passages, avoid catching a cold or to generally improve one's health to cite a few examples. Some people also claim that nasal lavage improves ones vision by cleaning the tear ducts, improves the sense of smell and improves ones sense of taste. Some nasal lavage products can include canisters containing rinse solution that may be under excessive pressure, causing solution flow to be somewhat uncomfortable during use.

SUMMARY

Systems and methods for dispensing fluid are described. In some implementations, a dispensing device is provided that includes a body portion surrounding a cavity; and a tip portion having a fluid path that is fluidly connected to the cavity, the tip portion having an internal actuator configured to cause fluid flow to exit the tip portion through the fluid path at a predetermined pressure level when the internal actuator is actuated.

DESCRIPTION OF DRAWINGS

FIGS. 2 and 3 are a schematic top view and a schematic plan view of a tip used on the device.

DETAILED DESCRIPTION

Figure 1:
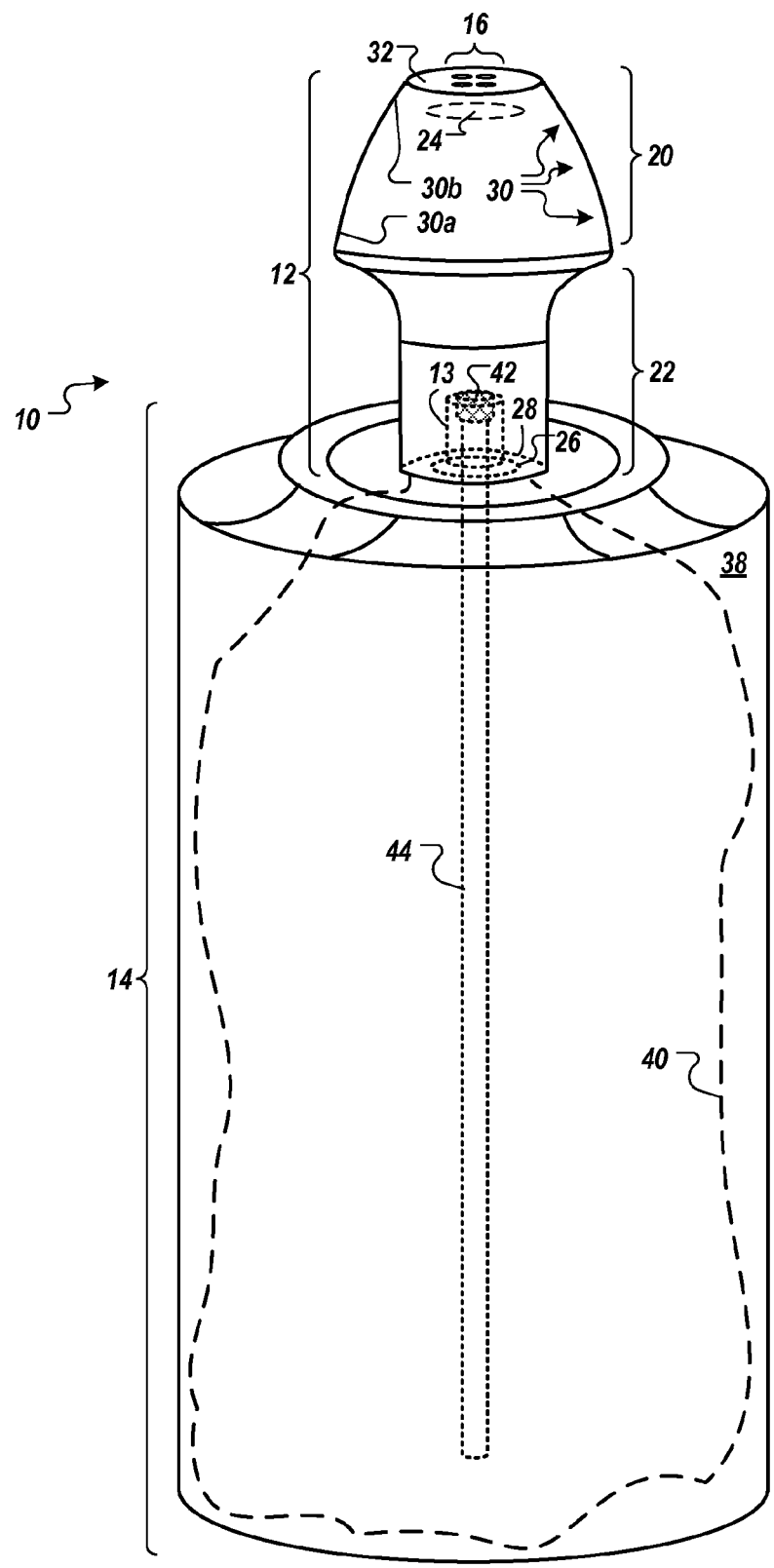
FIG. 1 is a schematic perspective view of a device.

Referring to FIG. 1, a fluid ejection device 10 is shown. The fluid ejection device 10 includes a tip 12 that is attached to an actuator 13, which in turn is attached to a body 14. The body 14 can be, for example, a container of saline solution or any other fluid suitable for irrigating cavities (e.g., nasal cavities). The fluid ejection device 10 can be used, for example, to provide nasal rinsing (or irrigation or lavage), such as to treat allergies, improve breathing, eliminate post-nasal drip or sinus infections, moisten dry nasal passages, etc. The tip 12 can attenuate the pressure of fluid stored in the body 14, dispensing fluid at a significantly more gentle pressure but at a higher volume or flow rate. The gentle pressure can be sufficient pressure to deliver a flow of fluid to nasal tissue without the pressure being so great as to apply an amount of pressure to the tissue to displace the tissue.

In some implementations, the body 14 can be a fluid container (e.g., can, canister, bottle, etc.) having bag-on valve technology where there is a bag inside the container and the valve can release the solution when the actuator is actuated, i.e., pressed. In some implementations, the fluid ejection device 10 can be used on a plastic bottle which is pressurized and has a solution inside the bottle. In some implementations, the fluid delivery is from an aerosol type can, but the fluid is ejected from the tip 12 in a fluid stream, rather than an aerosol.

The tip 12 can be operable to provide an attenuated pressure of fluid flow from the body 14. For example, the body 14 can be a commercially-available, pressurized container of saline solution or other sterile fluid which ordinarily dispenses fluid at a pressure that may be unsuitable, uncomfortable or unsafe for use in lavage. As such, the tip 12 can include features that facilitate the delivery of fluid in a generally more gentle stream through at least one (e.g., about four or more) apertures 16 at the end of the tip 12. Fluid flow can be controlled, for example, by pressing the tip 12. In some implementations, the tip 12 can be pressed straight against the nose, allowing fluid to flow from the tip. In some implementations, pressing the tip 12 from the side can control fluid flow.

The tip 12 includes a distal portion 20 and a proximate portion 22. In some implementations, the distal portion 20 of the tip 12 can be approximately conically shaped, with a convex curved surface leading from the apertures 16 toward the proximate portion 22. In some implementations, the distal portion 20 can be approximately gumdrop- or mushroom-shaped. The tip 12 can include a tapered surface 30 that permits the tip 12 to conform to the cavity that is to be rinsed, such as to conform to nostrils of different sizes. Specifically, the exterior of the tip 12 can be tapered outwardly along the distal portion 20. In some implementations, the tip 12 tapers from a wide portion 30$a$ up to a narrow portion 30$b$, where the narrow portion 30$b$ is closer to the apertures 16 than to the proximate portion 22. Moreover, the tip 12 can be sized to prevent the wide portion 30$a$ from extending all the way into the user's cavity (e.g., nostril).

The distal portion 20 can contain the features of the tip 12 that facilitate fluid flow, at an attenuated pressure, from the apertures 16. A stop 24 can be the ceiling of the interior fluid canal within the tip 12, positioned to block the fluid flow exiting the body 14, and causing the fluid flow to be redirected toward the proximate portion 22 of the tip 12. As a result, fluid can "pool" or otherwise accumulate inside the tip 12 and be dispensed at a reduced pressure through the apertures 16, while being replenished from fluid from the body 14 which dispenses at a higher pressure.

The apertures 16 can be arranged, for example, on a mesa 32 at the end of the distal portion 20. As depicted, the mesa 32 has a relatively flat surface, but other shapes (e.g., a convex shape) can be used that are effective at distributing the apertures 16 for efficient dispensing of fluid.

An aperture 26 in the proximate portion 22 can define the interior boundary of a collar 28 that surrounds, and securely attaches to, a portion of the actuator 13. In some implementations, if the actuator 13 is relatively small (e.g., a spray-paint can's spray button size), the aperture 26 can attach directly to the body 14. For example, the collar 28 can provide a snap-fit, screw-fit, or other such sealed connection between the proximate portion 22 (of the tip 12) and the body 14. However, when the actuator 13 is significantly larger, as it can be in some implementations, the tip 12 can attach directly to the actuator 13. In general, the tip 12 can be manufactured in various sizes or be adjustable to fit any size actuator 13 or body 14.

To aid in comfort of use, the tip 12 can be formed of a flexible material, such as silicone or another soft, flexible material (e.g., plastic, rubber, non-permeable cloth, etc.) that can generally feel comfortable against the user's skin. In some implementations, the tip 12 can have an exterior circumference of less than 2 cm, such as less than 1.5 cm, allowing it to fit snugly against, but not extend all the way into, an average sized user's nostril. The actuator 13 can be formed of a material that is significantly more rigid than the tip 12. As such, the actuator 13 can hold its shape during use.

The body 14 surrounds a chamber 38. The body 14 can be configured to resist a change in shape when pressure changes occur within the body 14 due to the contents of the chamber 38 moving/being expelled. For example, if the body 14 is formed of a generally rigid material (e.g., metal, such as steel or aluminum, plastic, such as a recyclable resin, such as polyethylene, polycarbonate or polypropylene, etc.), the body 14 can retain its shape when the chamber 38 is fully-pressurized (e.g., full of fluid), partially-pressurized, and essentially un-pressurized (e.g., when the fluid is essentially depleted).

In some implementations, the body 14 can include a bag 40 inside the chamber 38. The bag 40 can contain the fluid stored by the body 14 and can be formed of a flexible material, such as a pliable plastic. Further, the bag 40 can be hermetically sealed from the space between the body 14 and an exterior of the bag 40. As a result, using the bag 40 or a device similar to the bag-on valve technology (e.g., a pressurized can or pressurized bottle) can provide a sterile solution suitable for use in a body cavity or with a wound. As will be described in more detail below, the body 14 can include a valve 42 and a tube 44. The valve 42, such as any type of valve used on spray cans, can be used to control (e.g., start, stop, etc.) the flow of fluid from the chamber 38 to the tip 12. The fluid can flow through the tube 44 which can extend into the bottom end of the body 14, or the end that is most distal from the tip 12.

Referring to FIG. 2, an exemplary top view 50 of the fluid ejection device 10 is shown. The top view 50 shows the apertures 16a-16d arranged on the mesa 32, located on the tip of the distal portion 20. As depicted in FIG. 2, in some implementations, the centers of any pair of adjacent apertures 16a-16d are spaced at between about 1 and 4 millimeters, such as about 3 millimeters, as shown by distances 52a and 52b. Specifically, the distance 52a corresponds to the distance between the centers of apertures 16a and 16b. Similarly, the distance 52b corresponds to the distance between the centers of apertures 16c and 16d. The tip 12 can have an exterior circumference of less than 1.5 cm.

The diameters of the apertures 16a-16d can be any value (e.g., between about 1 and 2 millimeters, such as about 1.5 millimeters) such that, for example, the combination of the group of apertures 16a-16d produces a sufficient stream when the fluid ejection device 10 is in use. In some implementations, as the number of apertures is increased, the diameter of the apertures generally can be reduced.

In some implementations, different sizes of the apertures 16a-16d and/or other spacing between the apertures 16a-16d can be used, and fewer or additional apertures 16a-16d can exist, with varying distances between any of the apertures 16a-16d. In some implementations, distances 52a and 52b may be less than, or greater than, 3 millimeters. In some implementations, there are two, three, four, five or six apertures in the tip 12. The total cross sectional area of the apertures 16a-16d is generally less than the cross sectional area at any cross section of the canal 60 (e.g., having diameters 66 described with respect to FIG. 3) carrying the supply of fluid through the tip 12.

Referring to FIG. 3, an exemplary side cross-section view 56 of the fluid ejection device 10 is shown. The view 56 shows the tapered shape of the tip 12, including the tapered surface 30 that extends along the distal portion 20 toward its intersection with the proximate portion 22. The view 56 further shows a cross-section of the features of the interior of the tip 12. Fluid can flow through the tip 12 by entering a base area 57. For example, the base area 57 can include the collar 28 that serves as the connection point between the tip 12 and the actuator 13 and some adjacent region of the tip 12, such as a lower third of the tip. The collar 28 can surround or fit over a portion of the actuator 13, such as the portion of the actuator 13 from which fluid can flow. Fluid dispensed from within the chamber 38 can flow through the base area 57 and through the interior of the tip 12, exiting through the most distal end of the distal portion 20. In some implementations, the fluid can flow through the tube 44 and valve 42 (see FIG. 1).

The view 56 further shows internal features of the tip 12. A canal 60 in the interior of the tip 12 can provide fluid connectivity between the chamber 38 (e.g., via the actuator 13) and the apertures 16. Specifically, the canal 60 can extend from (and define the shape of) the aperture 26, defining the interior of the collar 24. The canal 60 can extend to, and be fluidly connected to, an annular chamber 62. In some implementations, a circular or cylindrical chamber 64 can exist, and be fluidly attached to, annular chamber 62 and canal 60. The canal 60 and the chambers 62 and 64 can work in combination, for example, based on their dimensions, to attenuate the pressure of the fluid received from the body 14 that flows through and exits the tip 12. For example, the fluid entering the tip 12 can generally pool within the canal 60, and the chambers 62 and 64 can facilitate the flow of the fluid through the tip 12 at suitable pressure through the apertures 16. For instance, the shape and size of the chambers 62 and 64 can restrict the flow of fluid to a volume that is ideal for delivery to the apertures 16.

Various dimensions of components of the tip 12 can exist. For example, the canal 60 can have a tapered shape, having dimensions that include, for example, a diameter 66a of in the range between about 5 and 9 mm, such as about 7 mm at the aperture 26, a diameter 66b of in the range between about 5 and 7 mm, such as about 6 mm roughly halfway up through the canal 60, and an even smaller diameter 66c such as in the range between about 4 and 6 mm, such as about 5.5 mm or less approaching the apertures 16. The annular chamber 62 can have, for example, an outer diameter 66d equal to or less than 66c, such as in the range between about 4 and 5.2 mm, such as about 4.6 mm and an inner diameter 66f of in the range between about 1 and 1.5 mm, such as about 1.3 mm. The circular chamber 64 can have a diameter 66e equal to or less than that of diameter 66c in the range between about 3 and 5 mm, such as about 3.7 mm. In some implementations, the diameter 64 is less than the outer diameter of chamber 62. The diameters 66a-66f are just examples, as other diameters can be used in other implementations.

Various other dimensions of components of the tip 12 can exist. For example, the circular chamber 64 can have a thickness 66g in the range between about 1 and 2 mm, such as about 1.5 mm. The annular chamber 62 can have a thickness 66h in the range between about 0.5 and 1.2 mm, such as about 0.8 mm. The region between the mesa 32 and the stop 24 at the end of the distal portion 20 can have a thickness 66i in the range between about 0.8 and 1.2 mm such as about 1 mm. The canal 60 can have a length 66j in the range of between about 20 and 30 mm, such as about 25 mm. These thicknesses and lengths can vary in other implementations; however the side wall integrity of the tip 12 needs to be maintained.

Internal features of the tip 12 can vary in size and proportion to each other, the advantages of which can include better control of pressure attenuation. For example, in some implementations, the external circumference of the annular chamber 62 can be greater than the circumference of the circular chamber 64. In some implementations, the greatest extent of the apertures 16 (e.g., the sum of the surface areas of the apertures 16) can be greater than an external circumference of the annular chamber 62. In some implementations, the circumference of the circular chamber 64 is less than the minimum circumference of the canal 60 by in the range between 0.5 mm and 1.5 mm, such as at least about 1.0 mm. In some implementations, the canal 60 can have an internal volume of in the range between 0.3 cm3 and 0.5 cm3, such as at least about 0.4 cm3. In some implementations, the combined area of the apertures 16 in the distal portion 20 of the tip 12 can be greater than an area of the circular chamber 64.

In some implementations, the total cross sectional area of apertures 16 is greater than the cross sectional area of the valve 42. Without being bound to any particular theory, liquid exits from chamber 38 at a high pressure, such as at a pressure greater than about 10 psi, such as in the range of 20 and 200 psi, such as at a pressure of greater than about 30 psi and enters canal 60 directed toward the apertures 16. The high pressure fluid contacts an end wall (e.g., the stop 24), which redirects the fluid toward aperture 26. Some fluid exits apertures 16 while canal 60 fills with fluid. Once the canal 60 fills, because the overall effective area of the apertures 16 area is greater than the valve 42 exit area in combination with the availability of fluid in the canal 60, the pressure of fluid exiting the chamber 38 is attenuated and the fluid exits the apertures 16 in a gentle contiguous stream.

Figure 4:
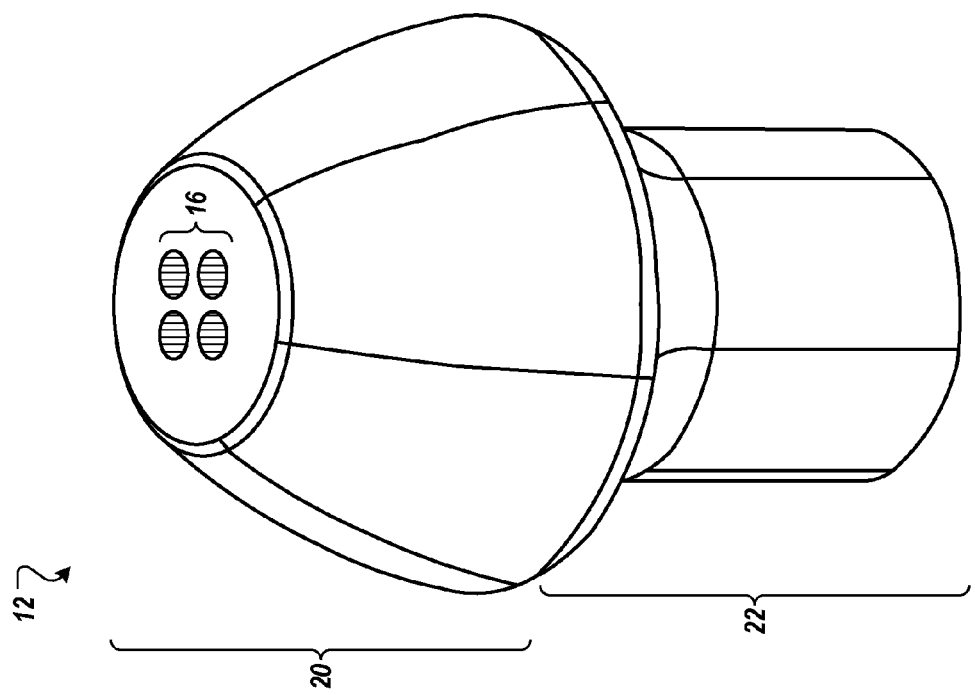

Referring to FIG. 4, a perspective view of the fluid ejection device 10 is shown. Although the implementation shown in FIG. 4 includes four apertures 16 of the same size, other implementations can include more (or fewer) of the apertures 16. Further, the apertures 16 can have various sizes and spacing, for example, as can be determined through experimentation to deliver a stream of fluid more suitable for lavage.

In some implementation, various models of the fluid ejection device 10 can exist, each having the advantage of a different configuration of apertures 16. For example, some users may prefer using a specific "Model X" over "Model Y" because of a difference in operation or "feel" of each, such as a noticeable difference in the strength of the stream of fluid from each. In some implementations, additional versions of the fluid ejection device 10 can have significantly larger tips 12 (e.g., for adults with significantly larger nostrils) or significantly smaller tips 12 (e.g., for babies or toddlers). As such, different models or versions of the fluid ejection device 10 can be produced.

Although implementations of the tip 12 and the fluid ejection device 10 are generally intended for human use, other implementations can include models or versions that are intended to use for animals, such as pets or livestock.

Figure 5:
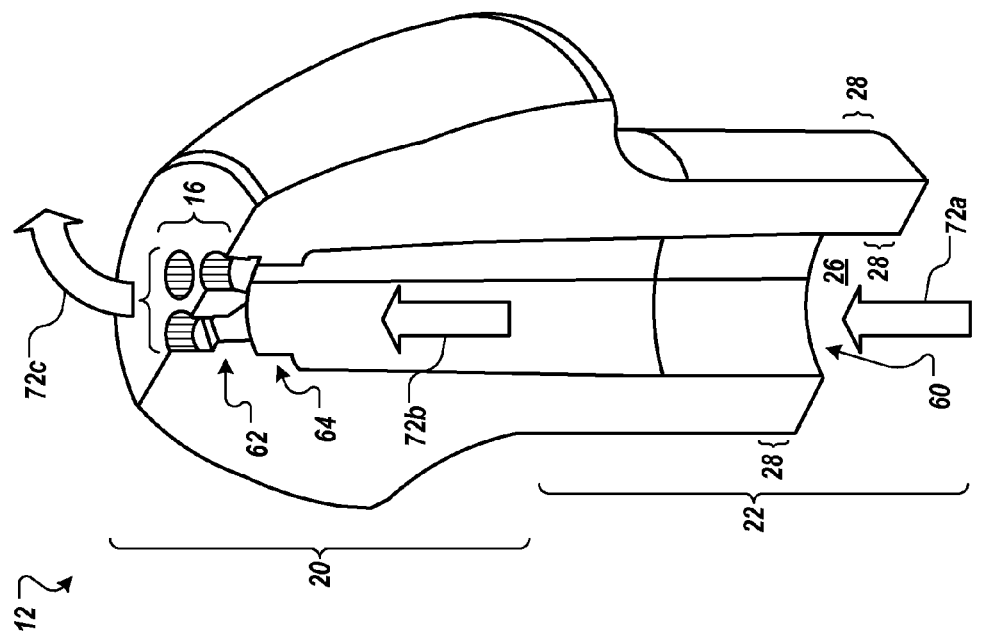
FIGS. 4 and 5 are schematic perspective views of a tip used on the device.

Referring to FIG. 5, a cross-section of a perspective view of the fluid ejection device 10 is shown. The view shows half of the tip 12 exposed, and as such exposes half of the distal portion 20 and the proximate portion 22, as well as revealing the canal 60.

Fluid can flow through the tip 12 in the direction indicated by arrows 72a-72c. Specifically, fluid from the body 14 can enter the tip 12, as indicated by arrow 72a. Fluid entering the tip 12 does so through the aperture 26, as defined by the inner dimension of the collar 28. Fluid flows through the canal 60, on the interior of the tip 12, as indicated by arrow 72c. Fluid exits the tip 12 at the apertures 16, as indicated by arrow 72c. Before reaching the apertures 16, the fluid can flow through the annular chamber 62, the circular chamber 64, and any other chambers not depicted.

Figure 6:
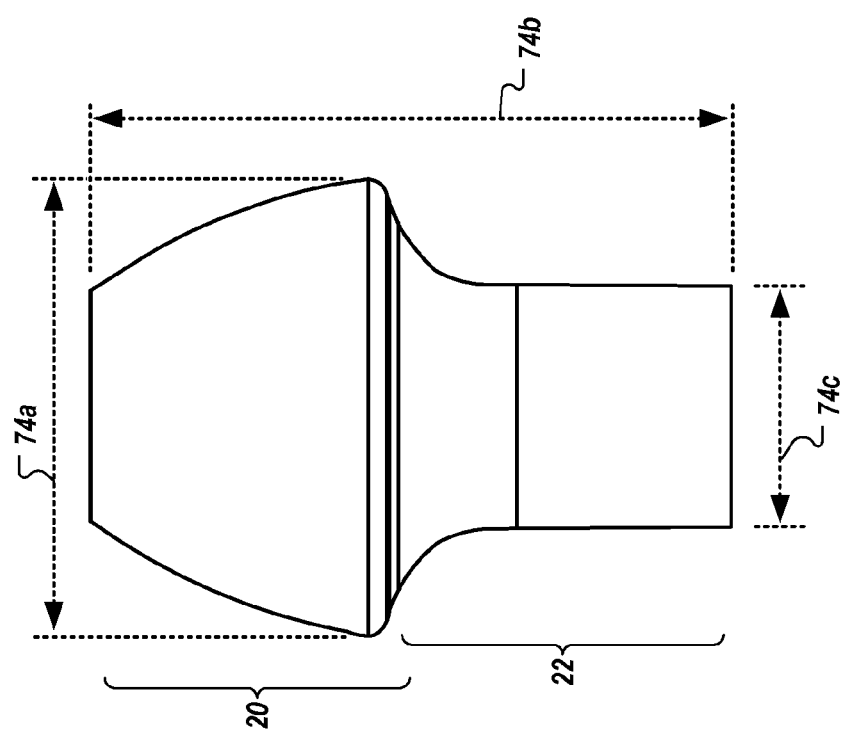
FIG. 6 is a schematic side view of the tip.

Referring to FIG. 6, exemplary dimensions of the tip 12 are shown. For instance, in some implementations, the diameter 74a of the widest part of the distal portion 20 (and of the tip 12 itself) can be, for example, in the range between 15 and 25 mm, such as about 20 mm or any other size that is suitable for use with human nostrils. In some implementations, the length 74b of the tip 12 can be, for example, in the range between 20 and 40 mm, such as about 30 mm, or any other suitable length. For instance, longer tips 12 can be necessary to fit different types of actuators 14, depending on the size of any exposed tube 44 and valve 42. The diameter 74c of the proximate portion 22 of the tip 12 can be, for example, in the range between 7 and 14 mm, such as about 10 mm, or any other size that can enable the tip 12 to fit the portion of the actuator 13 or body 14 to which the tip 12 is attached.

Figure 7:
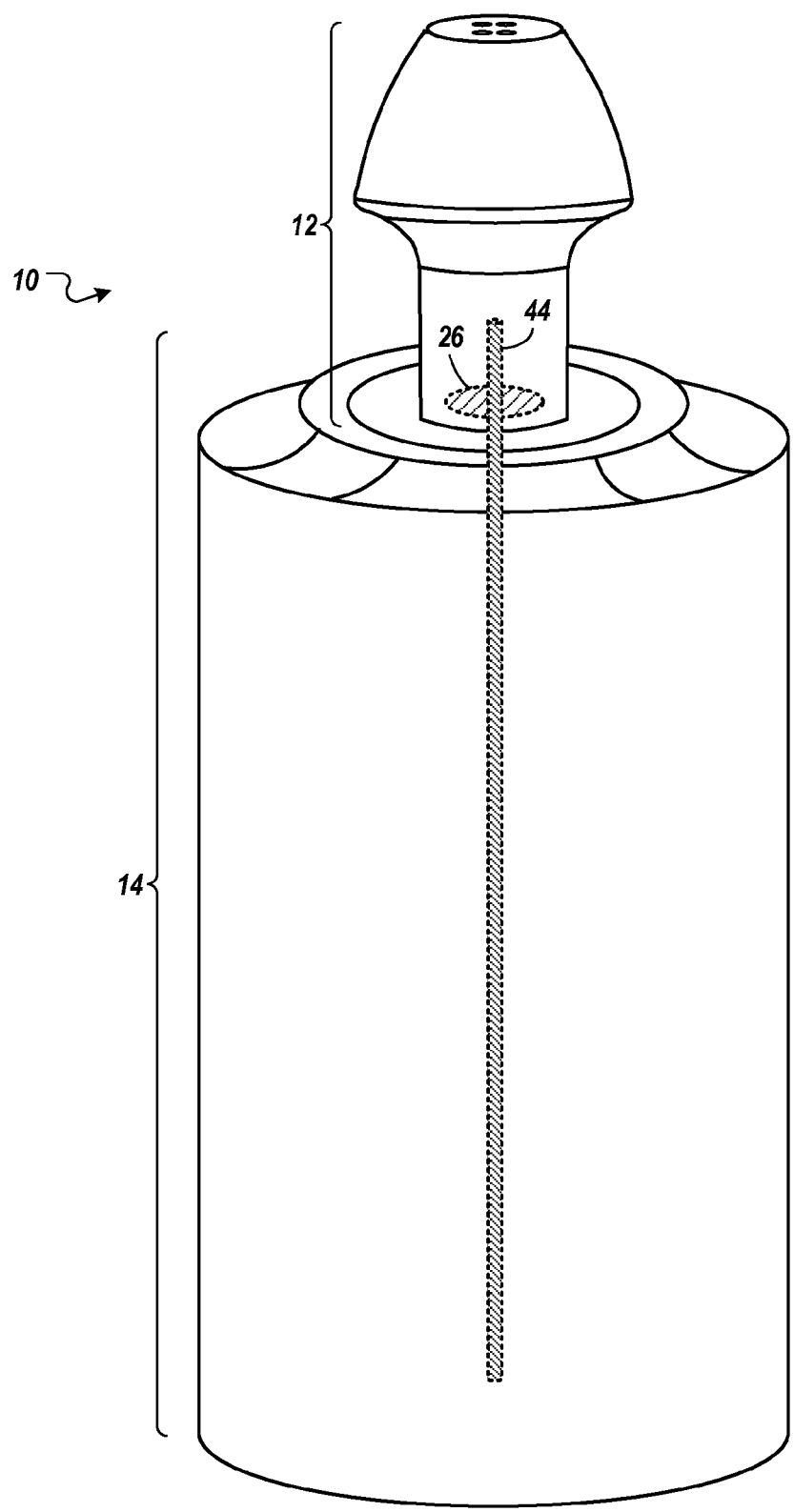
FIG. 7 is a schematic perspective view of the device.

Referring to FIG. 7, the fluid ejection device 10 is shown with the tip 12 covering the aperture 26 and the valve 42 which are both extruding from the body 14.

Figure 8:
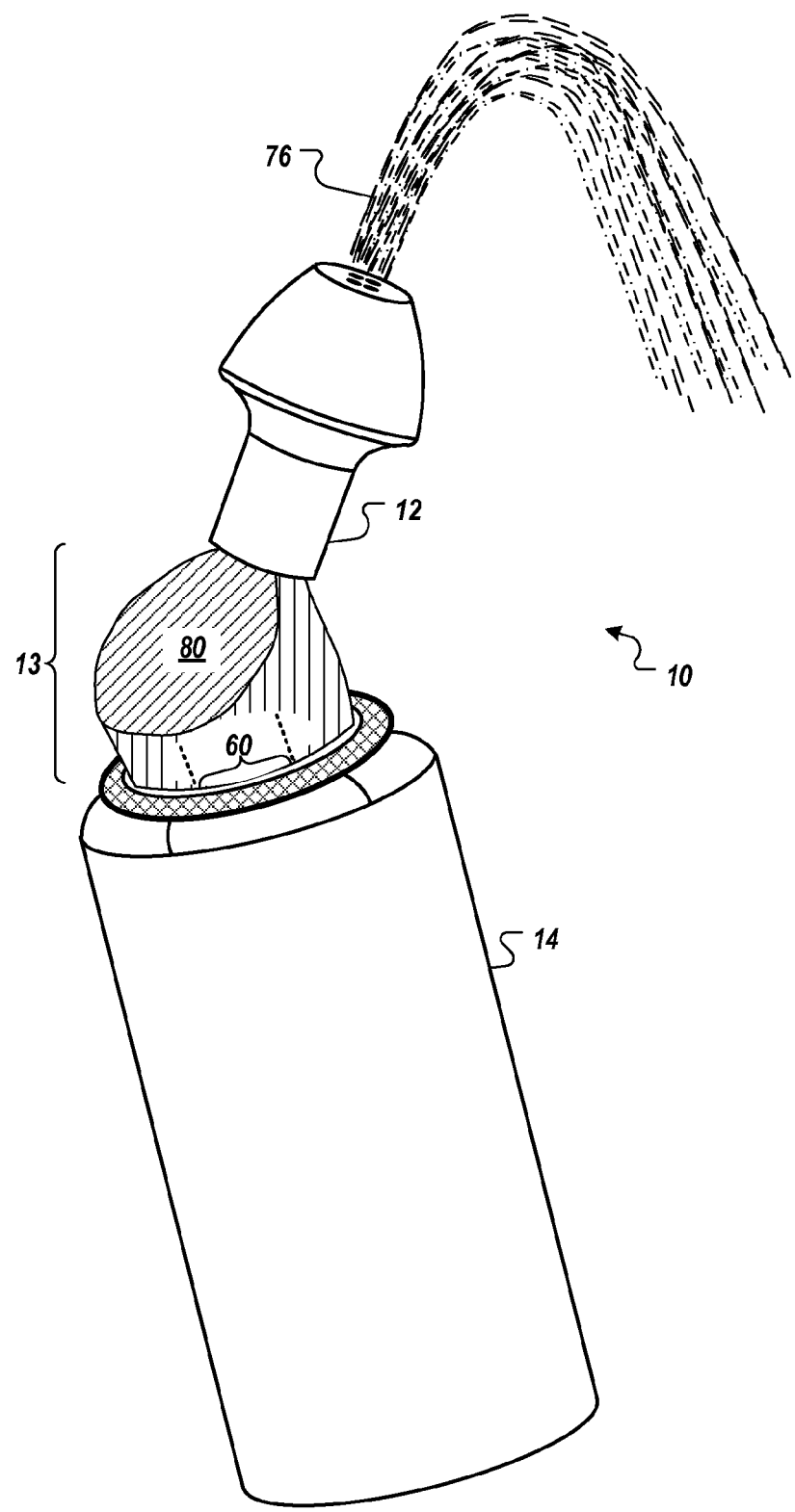
FIG. 8 is a schematic perspective view of the device in use.

Referring to FIG. 8, an exemplary stream of fluid 76 flowing from the fluid ejection device 10 is shown. The stream of fluid 76 can have a gentle arc, as depicted, due to the pressure-attenuating features of the tip 12. For example, while the fluid in the body 14 may be stored and released at a generally high pressure (e.g., too forceful for nasal lavage), the tip 12 can receive the fluid at high pressure, attenuate the pressure, and dispense the fluid at a lower pressure, but having a higher volume. In this way, the fluid stream can achieve an arc and flow as generally depicted by the stream of fluid 76. The stream of fluid 76 can exit the tip 12 along a trajectory that is substantially along a central axis of the canal 60. The apex of the arc of fluid occurs within a range of between about 4 and 12 cm, such as 8 cm, such as within 7 cm or within 5 cm of the apertures. In some implementations, fluid is ejected in a stream rather than ejected as a mist or as individual droplets.

In some implementations, the tip 12 can include, or be fluidly connected to, the actuator 13 that can be used to start and stop the flow of fluid from the body 14. The actuator 13 depicted here in FIG. 8 is larger than the embodiment of the actuator 13 depicted in FIG. 1. As such, the tip 12 can connect directly to the larger actuator 13.

Figure 9:
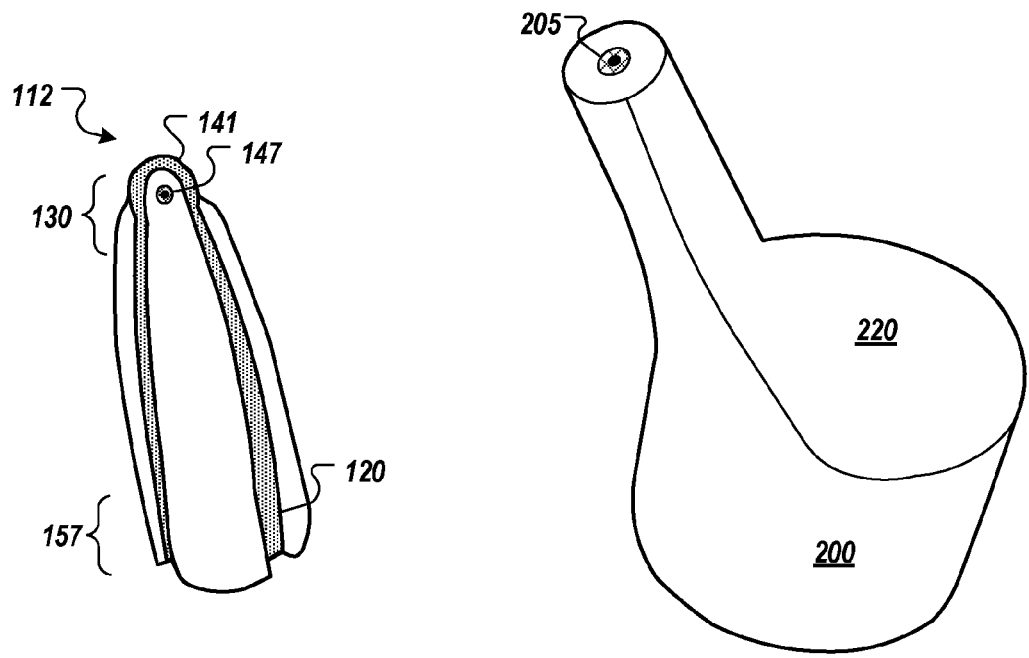
FIG. 9 is a perspective view of an implementation of a tip and actuator.
Figure 10:
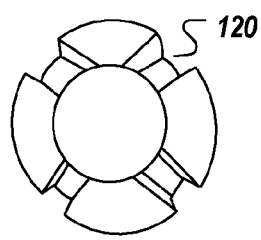
FIG. 10 is a top view of an implementation of a tip.

Referring to FIGS. 9 and 10, in some implementations, the tip 112 is approximately conically shaped from top to bottom. The tip 112 can have a base 157 with a circular inner diameter and an outer diameter that is either circular or approximately circular. Thus, the tip has an internal channel extending from the base 157 to an end upper region 130 of the tip 112. The tip 112 can include one or more grooves 120, such as two, three, four, five or six grooves. The grooves 120 can extend from the base 157 to the upper region 130 of the tip 112. In some implementations, the grooves extend at least 80% of the length of the tip 112. The tip has a thickness in the grooved area that is less than the thickness in the non-grooved area. Therefore, the grooved area can be more flexible than the non-grooved areas and can stretch more in a lateral direction, the lateral direction being perpendicular to the long axis of the internal channel, than the non-grooved areas.

Figure 11:
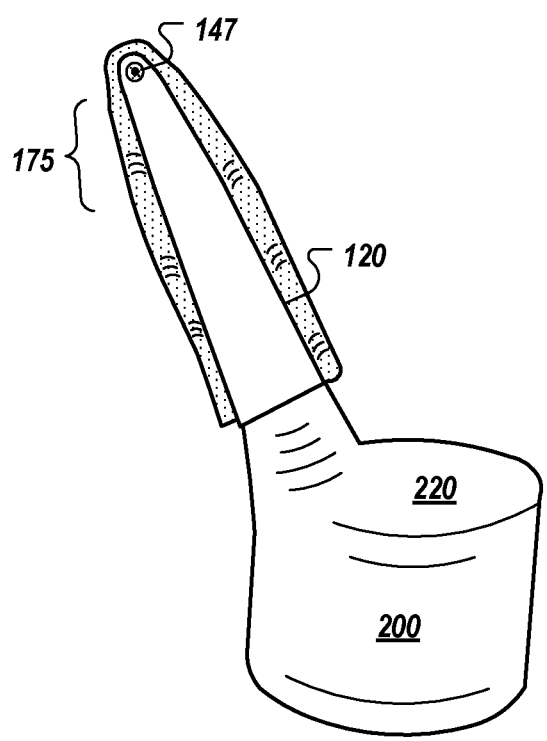
FIG. 11 is a side view of a tip on an actuator.

Referring to FIGS. 9 and 11, in some implementations, the upper region 130 of the tip has a smooth curved end 141. The upper region 130 of the tip can have one or more apertures 147 extending from the interior channel to the outer surface of the tip 112. In some implementations, the apertures 147 are not in the end 141, but are just below the end 141 and on the sides of the end 141. In some implementations, the apertures 147 are aligned with the thick portions of the tip 157 and not with the grooves 120. In some implementations, the tip 112 includes two apertures 147, each one directly across from one another so that the channel and the apertures together form a T-shape.

As with the first described tip, this tip can be formed of a flexible material, such as silicone or some another soft, flexible material (e.g., plastic, rubber, non-permeable cloth, etc.) that can generally feel comfortable against the user's skin. The actuator can be formed of a material that is significantly more rigid than the tip 112. As such, the actuator can hold its shape during use.

The tip 112 can fit over an actuator 200. The actuator can be similar to or the same as the actuator shown in FIG. 9. The actuator 200 has aperture 205 in its upper end. The aperture 205 is fluidly connected to a channel that extends the length of the actuator 200. The actuator 200 has a flat region 220 for depressing the actuator 200 and causing it to actuate a valve to which the channel is fluidly connected. The aperture 205 in the end of the actuator can be small, such as between 0.2 and 1 mm, e.g., around 0.4-0.6 mm in diameter. In some implementations, the aperture 205 in the actuator 200 is smaller than the apertures 147 in the tip 112.

Because of the flexibility of the tip 112, the tip can fit snugly around an end of the actuator. In some implementations, the snug fit is all around the circumference of the actuator. Thus, a liquid tight fit can be achieved around the actuator. In some implementations, at least 25%, such as at least 50%, for example, more than 60% of the tip length is over the actuator. This can prevent the tip from being pushed off of the actuator by the fluid pressure coming out of the dispenser. The shape of the actuator can be wider at the base than the tip. In some implementations, the tip has a cylindrical portion at a distal end, which transitions into widening portion that extends to the base. Because the tip can be flexible and stretch, the width of the tip can be equal to or smaller than the width of the actuator when the tip is not stretched or is in a relaxed state.

Between the end of the actuator and the apertures in the tip the channel forms a pocket 175 where fluid can pool before being pushed out of the apertures. The pocket 175 can have a length of between about 0.5 and 1.5 cm, such as around 1 cm. The pocket diameter can be between 0.2 and 0.6 cm.

In some implementations, the external diameter of the tip 112 at its base 157 is between 0.8 and 1.4 cm, such as between 0.9 and 1.2 cm. The thick regions of the tip 112 at the base 157 can be between 0.7 and 2 mm, such as around 1.7 mm. The thin regions, that is, the regions with the grooves, can be between 0.5 and 1 mm, such as about 0.7 or 0.8 mm. The length of the tip 112 can be between 2 and 5 cm, such as about 4 cm. The end of the tip 141 can be between 0.2 and 0.6 cm wide, such as about 0.4 cm. The apertures 147 can have a diameter of between about 0.6 and 1.5 mm, such as around 1 mm. The apertures 147 can be circular in shape. Other shapes are possible.

Unlike the tip shown in FIG. 8, the tip with the apertures on a side surface of the tip causes fluid to exit the tip at approximately a right angle to the longest length of the tip. During use of the fluid ejection device, a user can partially insert the tip into a nasal cavity. The fluid ejection device can be held, for example, is in the upright position, where the tip is generally above the body. Controlling the flow of fluid from the tip can be accomplished, for example, by pressing a flat-shaped button area, operable to engage (or disengage) the valve (not shown) inside the actuator when the button area is pressed (or released). This fashion of controlling fluid flow differs from that described with respect to FIG. 1 in which the entire tip can be pressed. In FIG. 1, fluid flow can be controlled, for example, by pressing downwardly or at an angle to a longitudinal axis of the tip. In some implementations, the tip can be pressed straight against the nose so that the actuator is effectively depressed, allowing the valve to open and fluid to flow from the tip. In some implementations, such as those shown in FIG. 8, the actuator can be depressed, such as with a finger, to cause solution to exit the tip. In some implementations, pressing the tip from the side actuates the valve and causes the fluid flow into the tip. Other implementations can include other controls, such as switches, levers, or electronic controls capable of opening and closing the valve. In some implementations, an additional control or button may exist that allows the valve to be locked in the open position. The tip can provide a gentler and more comfortable rinsing experience for a user.

Figure 12:
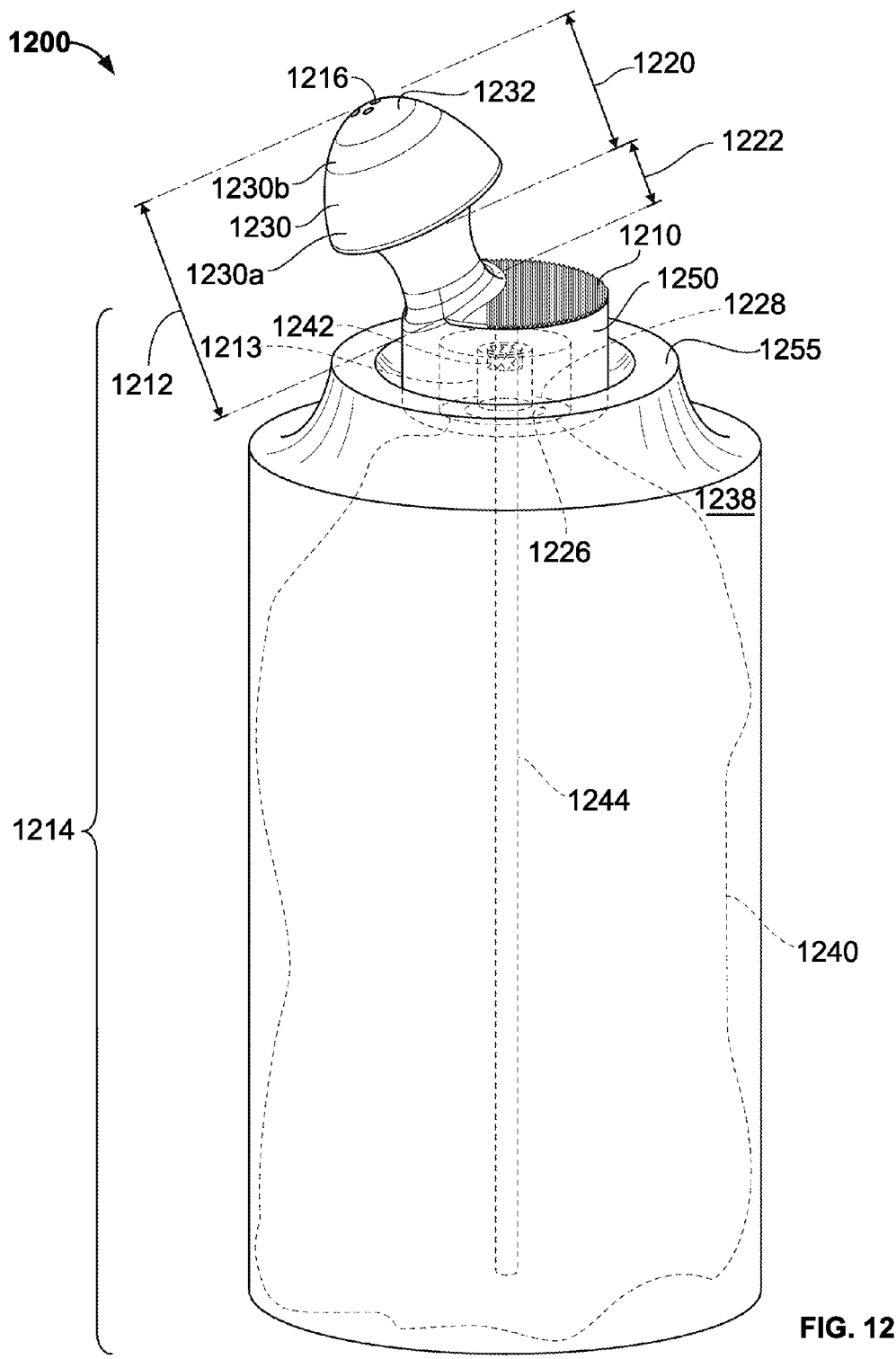
FIG. 12 illustrates a schematic perspective view of a device.

In some implementations, the tip (e.g., tip 12) and the actuator (e.g., 13) can be integrated into one piece. In some implementations, the tip can include an internal actuator configured to cause fluid flow to exit the tip (e.g., via apertures 16) through the fluid path (e.g., the canal 60) at a predetermined pressure level when the internal actuator is actuated. FIG. 12 illustrates a fluid ejection device 1200 that includes a tip integrated with an actuator.

Referring to FIG. 12, the fluid ejection device 1200 includes, a tip 1212, an actuator 1250 and a body 1214. The body 14 can be, for example, a container of saline solution or any other fluid suitable for irrigating cavities. The fluid ejection device 1200 can be used, for example, to provide nasal rinsing (or irrigation or lavage), such as to treat allergies, improve breathing, eliminate post-nasal drip or sinus infections, moisten dry nasal passages, etc. The actuator 1250 enables users to release the fluid stored in the body 1214. The actuator 1250 can include a texture surfaced structure 1210 that allows users to securely press down the actuator 1250 with fingers.

The tip 1212, which is integrated into the actuator 1250 (e.g., instead of attaching the tip to the actuator or fitting the tip over the actuator as shown in FIG. 11), can be used attenuate the pressure of fluid released by the actuator 1250, and dispense the fluid at a significantly more gentle pressure but at a higher volume or flow rate. The gentle pressure can be sufficient pressure to deliver a flow of fluid to nasal tissue without the pressure being so great as to apply sufficient pressure to the tissue to displace the tissue. In some implementations, the tip 1212 and the actuator 1250 can be viewed as a tip having an internal actuator. However, this view should not be construed as limiting, and that it is equally true that the fluid ejection device 1200 also can be seen to include an actuator having a tip.

In some implementations, the body 1214 can be a fluid container (e.g., can, canister, bottle, etc.) having bag-on valve technology where there is a bag inside the can and the valve can release the solution when the actuator 1250 is actuated (e.g., pressed). In some implementations, the fluid ejection device 1200 can be used on a plastic or metal bottle which is pressurized and has a solution inside the bottle. In some implementations, the fluid delivery is from an aerosol type can, but the fluid is ejected from the tip 1212 in a fluid stream, rather than an aerosol.

The tip 1212 can be operable to provide an attenuated pressure of fluid flow from the body 1214. For example, the body 1214 can be a commercially-available, pressurized container of saline solution or other sterile fluid which ordinarily dispenses fluid at a pressure that may be unsuitable, uncomfortable or unsafe for use in lavage. As such, the tip 1212 can include features that facilitate the delivery of fluid in a generally more gentle stream through at least one (e.g., about four or more) apertures 1216 at the end of the tip 1212. Fluid flow can be controlled, for example, by pressing the tip 1212. In some implementations, the tip 1212 can be pressed straight against the nose, allowing fluid to flow from the tip. In some implementations, pressing the tip 1212 from the side can control fluid flow.

The tip 1212 includes a distal portion 1220 and a proximate portion 1222. The distal portion 1220 of the tip 1212 can be approximately conically shaped, with a convex curved surface leading from the apertures 1216 toward the proximate portion 1222. In some implementations, the distal portion 1220 can be approximately gumdrop or mushroom shaped. The tip 1212 can include a tapered surface 1230 that permits the tip 1212 to conform to passages (e.g., nostrils) of different sizes. Specifically, the exterior of the tip 1212 can be tapered outwardly along the distal portion 1220. In the example shown, the tip 1212 tapers from a wide portion 1230a up to a narrow portion 1230b, where the narrow portion 1230b is closer to the apertures 16 than to the proximate portion 1222. Moreover, the tip 1212 can be sized to prevent the wide portion 1230a from extending all the way into the user's nostril.

The distal portion 1220 can contain the features of the tip 1212 that facilitate fluid flow, at an attenuated pressure, from the apertures 1216. The apertures 1216 can be arranged, for example, on a convex-shaped mesa 1232 at the end of the distal portion 1220. As depicted, the mesa 1232 has a relatively flat surface, but other shapes (e.g., a flat shape) can be used that are effective at distributing the apertures 1216 for efficient dispensing of fluid.

The texture surfaced structure 1210 can be cylindrically shaped to fit into the body 1214. The structure 1210 primarily connects the tip 1212 to the body 1214 so that fluids stored inside the body 1214 can communicate through a conduit 1244 into the structure 1210 and finally to the tip 1212. An aperture 1216 in the structure 1210 can define the interior boundary of a collar 1228 that surrounds, and securely attaches to, a portion of the body 1214. For example, the collar 1228 can provide a snap-fit, screw-fit, or other such sealed connection between the structure 1210 and the body 1214.

To aid in comfort of use, the tip 1212 can be formed of a flexible material, such as silicone or some another soft, flexible material (e.g., plastic, rubber, non-permeable cloth, etc.) that can generally feel comfortable against the user's skin. The tip 1212 can have an exterior circumference of less than 2 cm, such as less than 1.5 cm, allowing it to fit snugly against, but not extend all the way into, an average sized user's nostril. The structure 1210 can be formed of a material that is significantly more rigid than the tip 1212. As such, the structure 1210 can hold its shape during use. The overall actuator 1250 therefore can include different materials to fulfill its function while providing ergonomic comfort to users.

In some implementations, the diameter of the widest part of the distal portion 1220 (and of the tip 1212 itself) can be, for example, in the range between 15 and 25 mm, such as about 20 mm or any other size that is suitable for use with human nostrils. In some implementations, the length of the tip 1212 can be, for example, in the range between 20 and 40 mm, such as about 30 mm, or any other suitable length. The diameter of the proximate portion 1222 of the tip 1212 can be, for example, in the range between 7 and 14 mm, such as about 10 mm.

The body 1214 surrounds a chamber 1238. The body 1214 can be configured to resist a change in shape when pressure changes occur within the body 1214 due to the contents of the chamber 1238. For example, if the body 1214 is formed of a generally rigid material (e.g., metal, such as steel or aluminum; plastic, such as a recyclable resin, such as polyethylene, polycarbonate or polypropylene, etc.), the body 1214 can retain its shape when the chamber 1238 is fully-pressurized (e.g., full of fluid), partially-pressurized, and essentially unpressurized (e.g., when the fluid is essentially depleted).

In some implementations, the body 1214 can include a bag 1240 inside the chamber 1238. The bag 1240 can contain the fluid stored by the body 1214 and can be formed of a flexible material, such as a pliable plastic. Further, the bag 1240 can be hermetically sealed from the space between the body 1214 and an exterior of the bag 1240. As a result, using the bag 1240 or a device similar to the bag-on valve technology (e.g., a pressurized can or pressurized bottle) can provide a sterile solution suitable for use in a body cavity or with a wound.

As will be described in more detail below, the body 1214 can include a valve 1242 and a tube 1244. The valve 1242, such as any type of valve used on spray cans, can be used to control (e.g., start, stop, etc.) the flow of fluid from the chamber 1238 to the actuator 1250. The valve 1242 may be surrounded by an opening 1213 that fit with the actuator 1250; and allow the actuator 1250 to be partially surrounded by a supportive circumference 1255 of the body 1214. The fluid can flow through the tube 1244 which can extend into the bottom end of the body 1214, or the end that is most distal from the actuator 1250.

Figure 13:
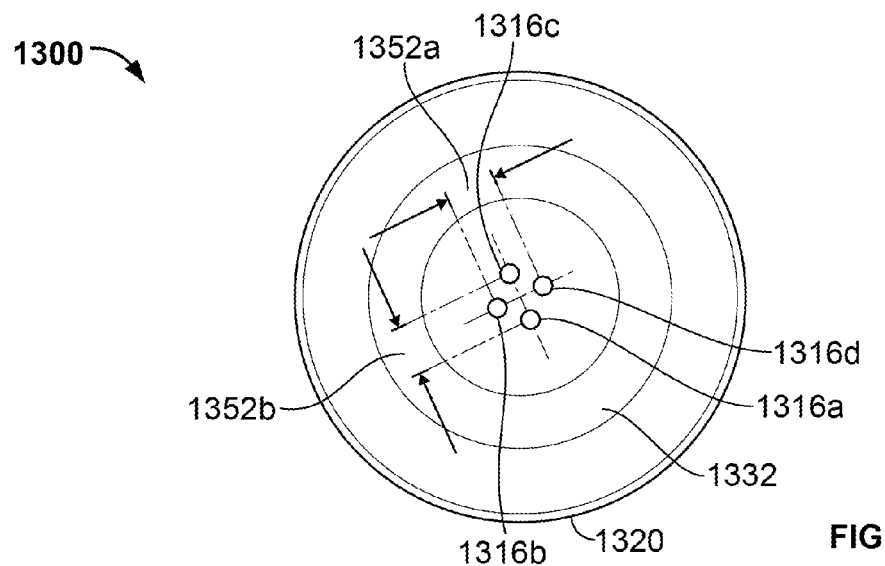
FIG. 13 illustrates a schematic view facing towards the ejection direction of a nasal rinse assembly on the device.

Referring to FIG. 13, an exemplary view 1300 facing towards the ejection direction of the tip 1220 of the fluid ejection device 1200 is shown. In this example, the view 1300 shows apertures 1316a-1316d arranged on a convex shaped mesa 1332, located on the tip of a distal portion 1320. Comparing to FIG. 12, the apertures 1316a-1316d can be the same as the apertures 1216, the mesa 1332 can be the same as the mesa 1232 and the distal portion 1320 can be the same as the distal portion 1220.

As depicted in FIG. 13, in some implementations, the centers of any pair of adjacent apertures 1316a-1316d are spaced at between about 1 and 4 millimeters, such as about 3 millimeters, as shown by distances 1352a and 1352b. Specifically, the distance 1352a corresponds to the distance between the centers of apertures 1316b and 1316d. Similarly, the distance 1352*b* corresponds to the distance between the centers of apertures 1316*a* and 1316*c*. The tip 1212 can have an exterior circumference of less than 1.5 cm.

The diameters of the apertures 1316*a*-1316*d* can be any value (e.g., between about 1 and 2 millimeters, such as about 1.5 millimeters) such that, for example, the combination of the group of apertures 1316*a*-1316*d* produces a sufficient stream when the fluid ejection device 1200 is in use. In some implementations, as the number of apertures is increased, the diameter of the apertures generally can be reduced. In some implementations, different sizes of the apertures 1316*a*-1316*d* and/or other spacing between the apertures 1316*a*-1316*d* can be used, and fewer or additional apertures 1316*a*-1316*d* can exist, with varying distances between any of the apertures 1316*a*-1316*d*. In some implementations, distances 1352*a* and 1352*b* may be less than, or greater than, 3 millimeters. In some implementations, there are two, three, four, five or six apertures in the tip 1212. In some implementations, the size of the apertures varies on a single device (i.e., not all apertures are required to be the same size or be spaced by a same amount).

Figure 14A:
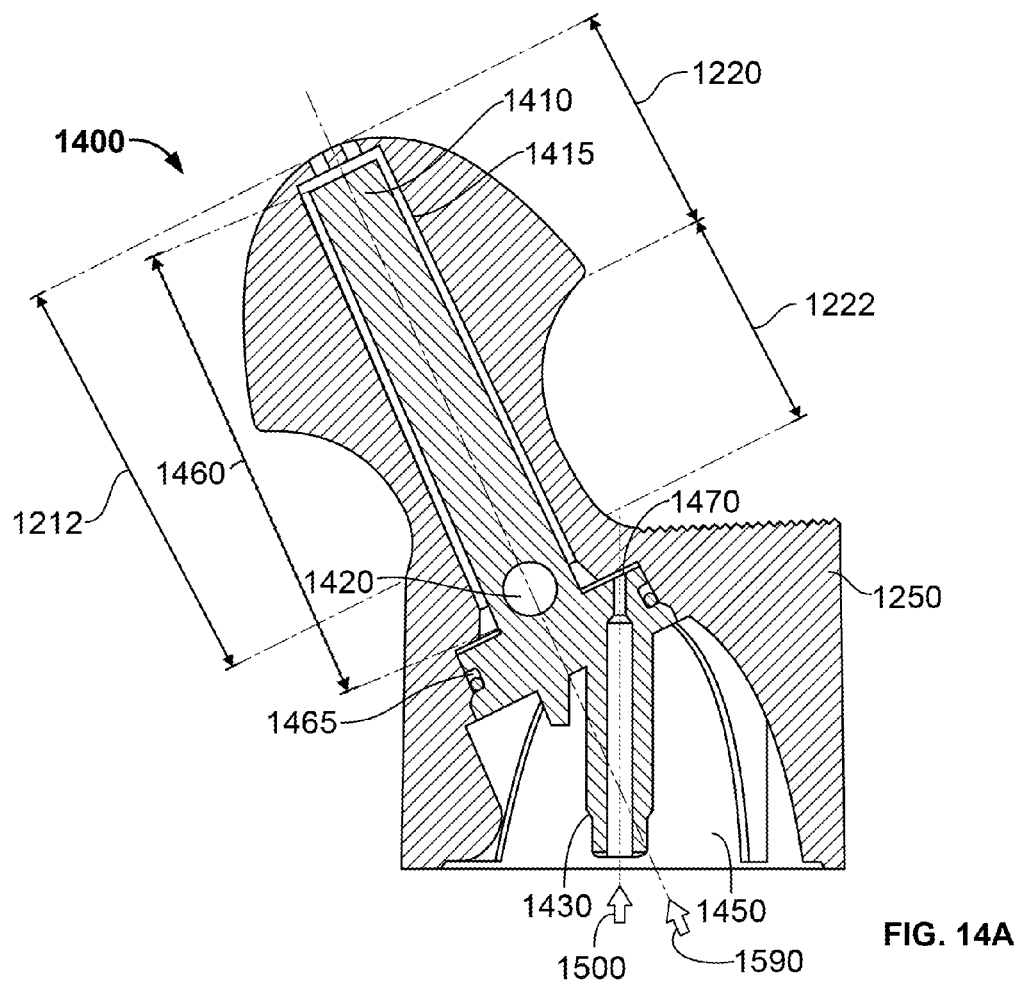
FIG. 14A illustrates a schematic cross-section view of the nasal rinse assembly.

Referring to FIG. 14A, an exemplary side cross-section view 1400 of the actuator assembly 1250 is shown. From the view 1400, the actuator 1250 includes an external shell 1210 and an internal component 1410. The external shell 1210 has been discussed as the texture surfaced structure 1210 in previous FIGS. 1 and 2. The features of the interior 1410 will be elaborated in the following as well as in FIG. 14B, which illustrates a schematic prospective view of the inner component 1410 of the rinse assembly.

The view 1400 shows the tapered shape of the tip 1212, including the tapered surface that extends along the distal portion 1220 toward its intersection with the proximate portion 1222. The view 1400 further shows a cross-section of the features of the interior 1450 of the texture surfaced structure 1210. Fluid can flow through the tip 1212 by entering a base tube 1430 of the inner component 1410. For example, the base tube 1430 can couple with the body 1214 and be actuated by displacing downwards to open the valve 1242 of the body 1214 and to release pressurized fluid through the conduit 1244 (FIG. 12). Fluid dispensed from within the chamber 1238 can flow through the base tube 1430 and through the interior 1410 of the tip 1212, exiting through the most distal end of the distal portion 1220.

The view 1400 further shows internal features of the structure 1250. A canal 1415 in the interior of the tip 1212 can provide fluid connectivity between the tube 1430 and the apertures 1316. The canal 1415 is formed from the clearance between the inner chamber of the tip 1212 and the extruding portion of the inner component 1410. In some implementations, the shape of the inner chamber of the tip 1212 and the extruding portion of the inner component 1410 can be identical or of different sizes. For example, the inner chamber of the tip 1212 can be of a cylindrical shape but slightly larger than that of the extruding portion of the inner component 1410. Specifically, the canal 1415 can extend from the apertures 1316 to the most distal position of the proximate portion 1222.

The view 1400 also shows detail features of the inner component 1410. The component 1410 includes an extrusion portion 1460, a sealing portion 1465, and the base tube 1430. The extrusion portion 1460 can be shaped as a tapered cylinder with the base portion connecting to the sealing portion 1465 wider than the tip portion. In some implementations, the extrusion portion 1460 can be substantially 26 mm in length. The tip of the extrusion portion can be a circular mesa of a substantially 4 mm diameter. The extrusion portion 1460 can taper at substantially 2 degrees and increase its cross-sectional diameter towards the sealing portion 1465. Approximately tangential to the sealing portion 1465, a cylindrical cavity 1420 is formed inside the extrusion portion 1460. The cavity 1420 extends in a direction as shown in FIG. 14A, but it may also extend in other directions. The cavity 1420 can be a cylindrical shape of substantially 3 mm diameter.

The sealing portion 1465 can couple with the internal chamber of the actuator 1250 to form the passage that allows fluid to substantially sealingly communicate from the base tube 1430 to the apertures 1316. The sealing portion 1465 includes a stepped structure for sealing and an orifice 1470 connected to the base tube 1430 for attenuation and regulation of the fluid pressure. The stepped structure may include a groove that can install a rubber ring for improved sealing. In some implementations, the orifice 1470 can be a cylindrical hole of a substantially 0.6 mm diameter, connected to the internal cylindrical portion of the base tube 1430. The internal cylindrical portion of the base tube 1430 can be substantially 1.5 mm in diameter and about 13 mm in total length. A gradual transition, such as a chamfer or a rounded step, may exist at the connection between the orifice and the inner cylindrical portion. The external diameter of the base tube 1430 can be substantially 3.5 mm in diameter, or any dimension that ensures the structural integrity to withstand internal pressure as well as external compression loading.

During operation, a user may press down the actuator 1250 by asserting a force towards the body 1214 on the textured surface, which may be made of any texture that increases the friction between the user's skin and the actuator 1250. As the actuator displaces towards the body 1214, the valve 1242 opens and the pressurized fluid ejects from the chamber 1238 into the base tube 1430. Simultaneously, the compression against the body 1214 allows the actuator 1250 to form a seal with the inner component 1410 at the sealing portion 1460. The fluid travels through the inner cylindrical portion of the base tube 1430 into the orifice 1470, then into the canal 1415. The cavity 1420 may serve as a buffer for pressure release as well as a reservoir storing extra fluid. After the canal 1415 and the cavity 1420 are filled with the fluid, the fluid will be ejected through the apertures 1216.

Figure 14B:
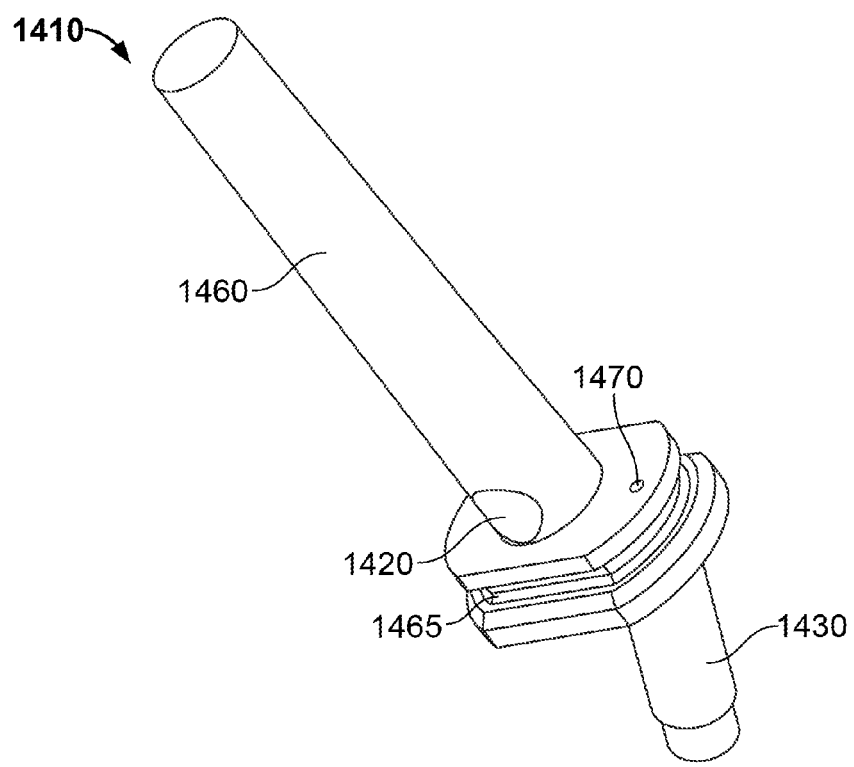
FIG. 14B illustrates a schematic prospective view of an inner component of the nasal rinse assembly.

Referring to FIG. 14B, a schematic perspective view of the inner component 1410 is illustrated. The inner component 1410 can be made of any material, such as a polymer, that enables its functions, such as retaining the shape during operation without excessive deformation. In some implementations, the inner component 1410 can be made of synthetic rubber, Bakelite, neoprene, nylon, PVC, polystyrene, polyethylene, polypropylene, polyacrylonitrile, PVB, silicone, or other such materials. In some implementations, the inner component 1410 is made of polymers that are of medium to low elastic modulus, which enables the sealing at the sealing portion 1465. The inner component 1410 may be made of a same or different material as the textured surface structure 1210. In this particular implementations, the textured surface structure 1210 is made of another harder material that can avoid excessive deformation from greater external forces and form a slippery surface for hygienic reasons.

Referring to FIGS. 12, 13, 14A and 14B, in some implementations, the total cross sectional area of apertures 1216 is greater than the cross sectional area of the valve 1242. Without being bound to any particular theory, liquid exits from chamber 1238 at a high pressure, such as at a pressure greater than about 10 psi, such as in the range of 20 and 1300 psi, such as at a pressure of greater than about 30 psi and enters canal 1415 directed toward the apertures 1216. The high pressure fluid contacts an end wall (e.g., the stop 24), which redirects the fluid toward aperture 1216. Some fluid exits apertures 1216 while canal 1415 fills with fluid. Once the canal 1415 fills, because the overall effective area of the apertures 1216 area is greater than the valve 1242 exit area in combination with the availability of fluid in the canal 1415, the pressure of fluid exiting the chamber 1238 is attenuated and the fluid exits the apertures 1216 in a gentle contiguous stream. Referring to FIG. 12, a perspective view of the fluid ejection device 1200 is shown. Although the implementation shown in FIG. 13 includes four apertures 1316 of the same size, other implementations can include more (or fewer) of the apertures 1316. Further, the apertures 1316 can have various sizes and spacing, for example, as can be determined through experimentation to deliver a stream of fluid more suitable for lavage.

In some implementations, various models of the fluid ejection device 1200 can exist, each having the advantage of a different configuration of apertures 1216. For example, some users may prefer using a specific "Model X" over "Model Y" because of a difference in operation or "feel" of each, such as a noticeable difference in the strength of the stream of fluid from each. In some implementations, additional versions of the fluid ejection device 1200 can have significantly larger tips 1212 (e.g., for adults with significantly larger nostrils) or significantly smaller tips 1212 (e.g., for babies or toddlers). As such, different models or versions of the fluid ejection device 1200 can be produced. Although implementations of the tip 1212 and the fluid ejection device 1200 are generally intended for human use, other implementations can include models or versions that are intended to use for animals, such as pets or livestock.

Figure 15A:
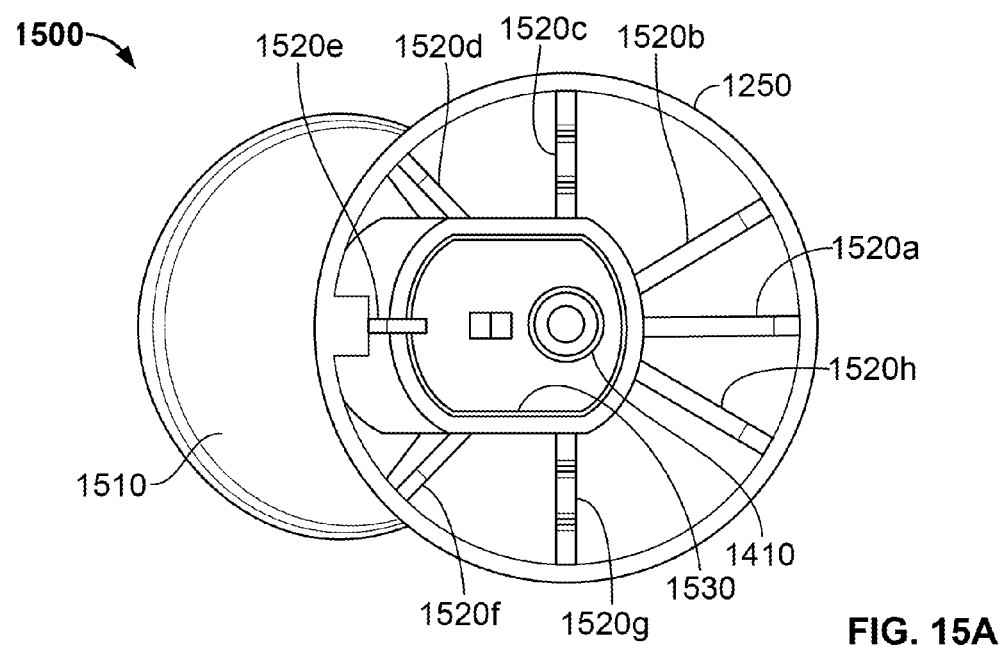
FIGS. 15A and 15B illustrate schematic bottom views of the nasal rinse assembly from two primary directions.
Figure 15B:
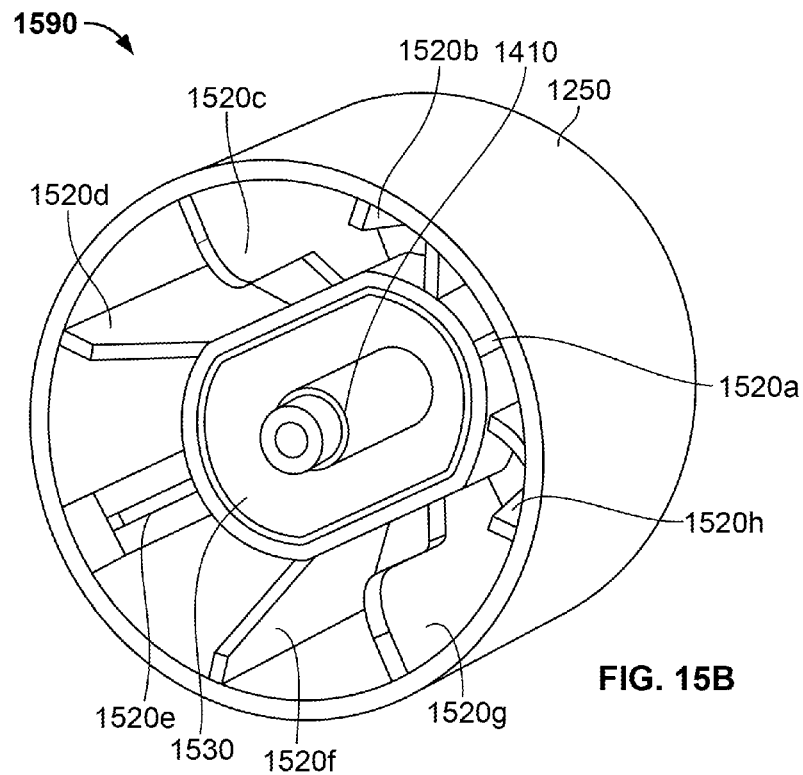

Referring to FIGS. 15A and 15B, schematic bottom views of the nasal rinse assembly from two primary directions are shown. The two primary directions are described in FIG. 14A as 1500 and 490. Referring first to FIG. 15A, the view in direction 1500 that is parallel to the longitudinal axis of the base tube 1430. In order to enable efficient assembly, the texture surfaced structure 1210 has an asymmetric housing 1530 for insertion of the inner component 1410. The inner component 1410 may have a holding structure that allows for clamping or holding by a human or robotic assembler. The housing 1530 is structurally supported by eight radial ribs 1520a-1520h. The ribs 1520a-1520h are designed so that the housing 1530 and the textured surface structure 1210 are one under normal use, while minimizing the material use in the structure. The tip 1510 is the same as the tip portion 1212 and can be used to guide the installation of the inner component 1410.

Now referring to FIG. 15B, another view is shown in the direction 490 that is parallel to the longitudinal axis of the extrusion portion 1460. In some implementations, FIG. 15B shows exemplar rib designs regarding each relative position to the housing 1530. For example, rib 1520a has an arc shape due to its furthest distance from the housing 1530. The rib 1520c and 1520g extends vertically so that attaching to another structure is made possible. The rib 1520e is short but reinforced to give enough support to the housing 1530. Depending on the material used, the rib design may vary without geometric limitation when performing the same structural function.

Figure 16:
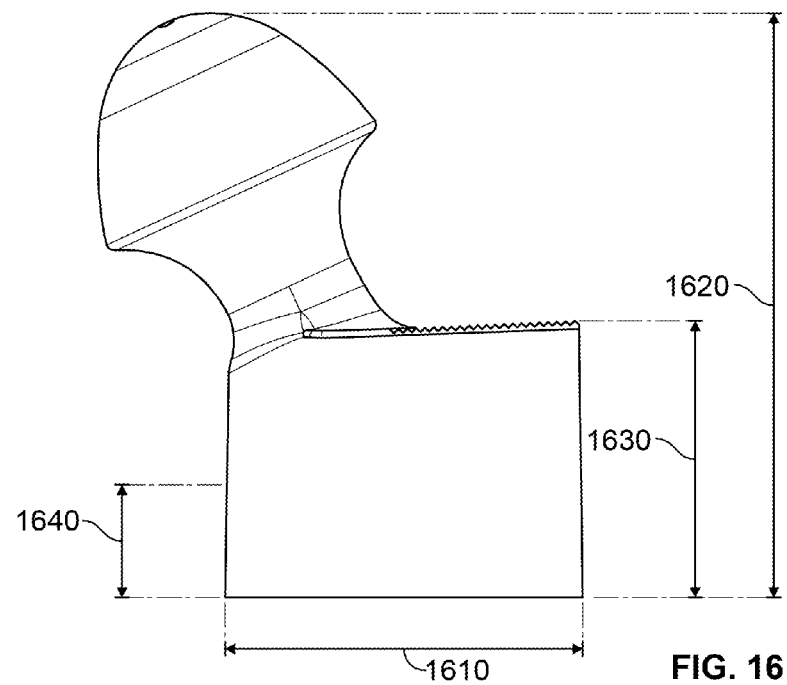
FIG. 16 illustrates a schematic side view of the nasal rinse assembly exterior.

Referring to FIG. 16, exemplary dimensions of the actuator 1250 are shown. For instance, in some implementations, the diameter 1610 of the widest part of the structure 1210 can be, for example, in the range between 15 and 35 mm, such as about 24 mm or any other size that is suitable for use with the body 1214. In some implementations, the overall height 1620 of the actuator 1250 can be, for example, in the range between 20 and 60 mm, such as about 40 mm, or any other suitable length depending on various tips for various nostril sizes. For instance, longer tips can result in a larger dimension. The height 1630 of the textured surface measured from the bottom of the actuator 1250 can be, for example in the range between 15 and 30 mm, such as about 18 mm, or any other suitable height to fit with the body 1214 and convenient for fingers to reach. A mark can be embossed on the side wall of the structure 1210, at a height of 1640, which can be in the range between 1 and 60 mm, such as 6.5 mm, to show logo, trademark, brand name, slogan, warnings or other important information.

Figure 17:
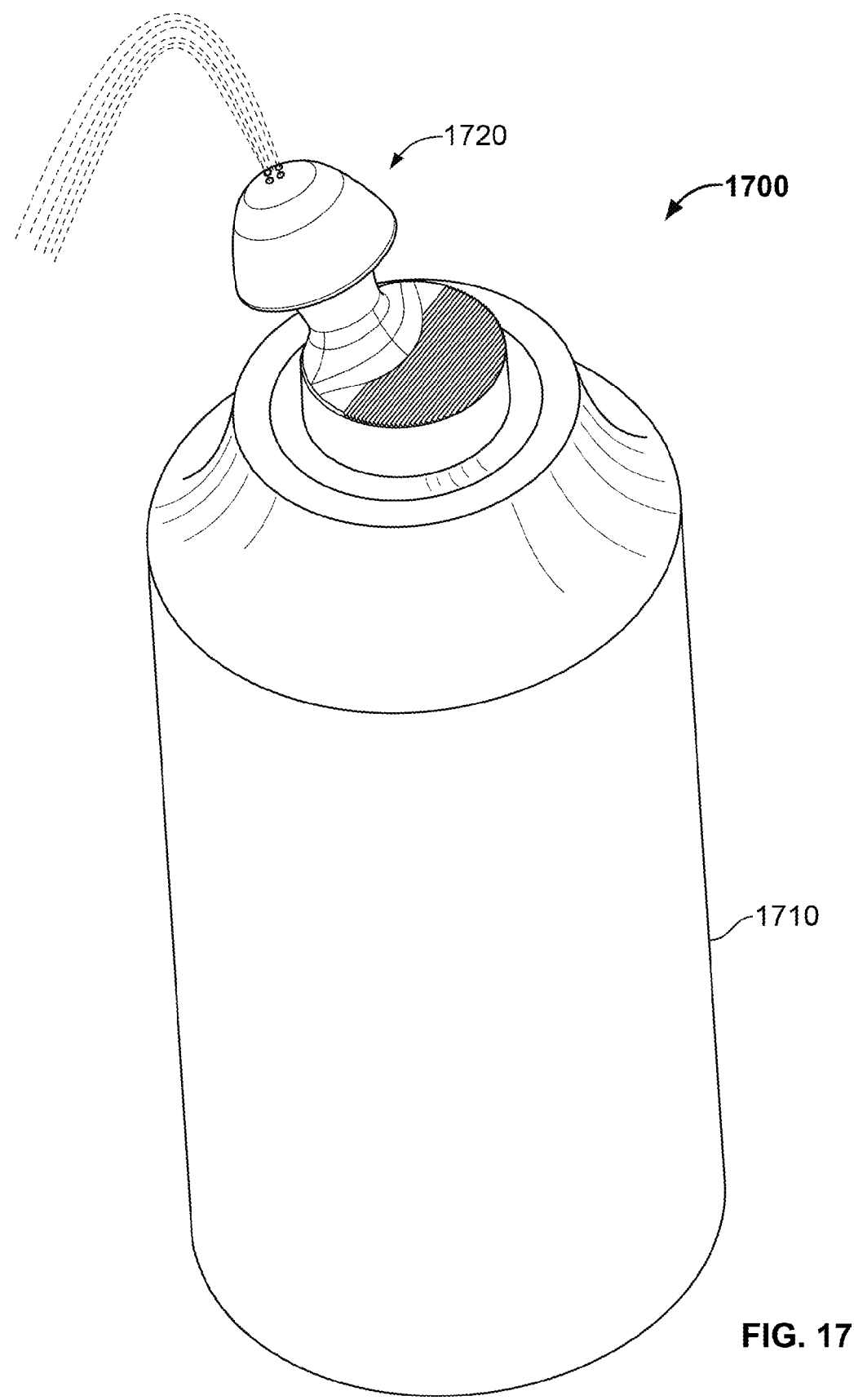
FIG. 17. illustrates a schematic view of the device in use.

Referring to FIG. 17, an exemplary stream 1700 of fluid flowing from the fluid ejection device 1200 that includes a body 1710 and an actuator 1720 is shown. The body 1710 can be a can of any formable material (e.g., plastic) containing fluid. The body 1710 may contain pressurized fluid or unpressurized fluid. The actuator 1720 may be used to open a valve in the body 1710 to release the pressurized fluid or may be used to actuate a pressurizing mechanism inside the body 1710 to eject the original unpressurized fluid. The stream of fluid 1700 can have a gentle arc, as depicted, due to the pressure-attenuating features of the actuator 1250. For example, while the fluid in the body 1214 may be stored and released at a generally high pressure (e.g., too forceful for nasal lavage), the tip 1212 of the actuator 1250 can receive the fluid at high pressure at the base tube 1430, attenuate the pressure inside the actuator 1250, and dispense the fluid at a lower pressure through the apertures 1216, but having a higher volume. In this way, the fluid stream can achieve an arc and flow as generally depicted by the stream of fluid 1700. The stream of fluid 1700 can exit the tip 1212 along a trajectory that is along a central axis of the canal 1415. The apex of the arc of fluid occurs within a range of between about 4 and 12 cm, such as 8 cm, such as within 7 cm or within 5 cm of the apertures. In some implementations, fluid is ejected in a stream rather than ejected as a mist or as individual droplets.

Figure 18A:
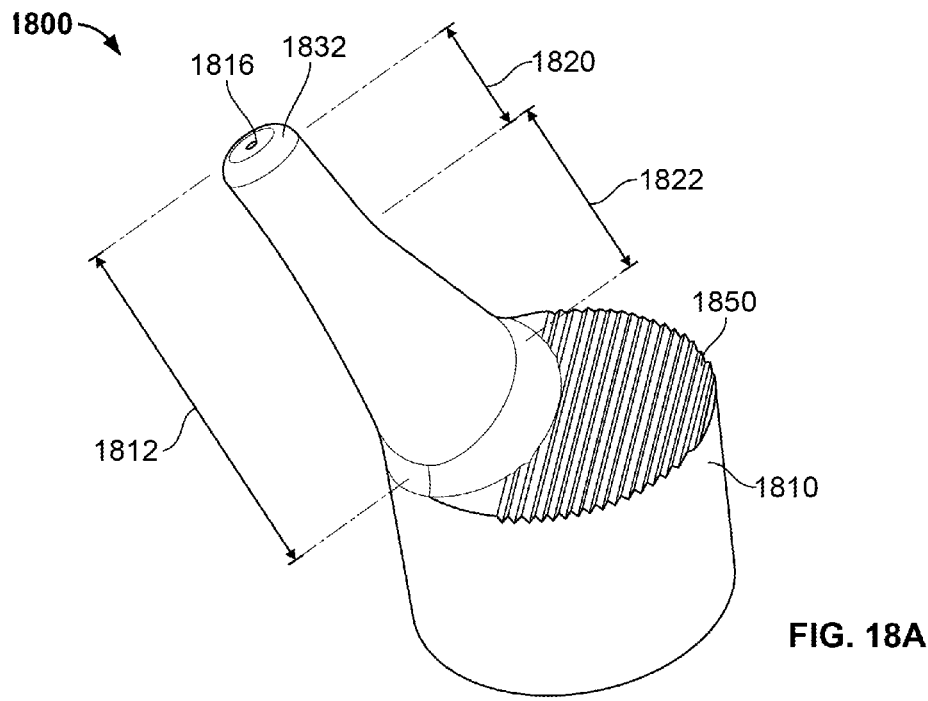
FIGS. 18A and 18B illustrate schematic perspective views of variations of the nasal rinse assembly.
Figure 18B:
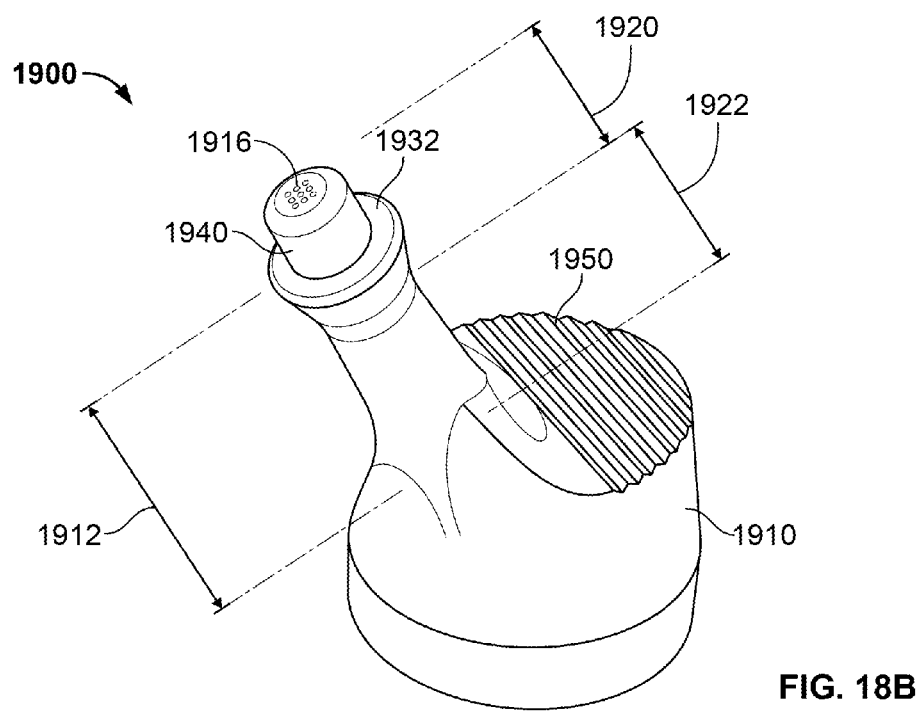

Referring to FIGS. 18A and 18B, in some implementation, various models of the actuator 1250 can exist, each having the advantage of a different configuration of the tip portion 1212 for ejecting fluid at different speeds and volumes. These models may use the same inner component 1410 to enable efficient production, assembly and quality control. In FIG. 18A, the view 1800 shows an actuator 1850 that can eject a medium strip of fluid to cleanse, moisturize or sooth passages. Similar to the actuator 1250, the actuator 1850 includes a textured body structure 1810 and a tip 1812 that includes an upper portion 1820 and a proximate portion 1822. The upper portion 1820 may have dimensions that allow the piece completely inserted into a user's nostril. For example, the upper portion 1820 may be a cylindrical shape that has a diameter smaller than an average size of human nostrils at the age of 5. At the end of the upper portion 1820, there is an aperture 1816 on a mesa 1832. The aperture 116 can be substantially similar to the aperture 1216. The proximate portion 1822 connects the upper portion 1820 to the body structure 1810 and operates with the inner component 1410 to generate desired fluid pressure and volume. In some implementations, the actuator 1850 attenuates the fluid pressure further for ejection of a medium stream through the aperture 1816.

In FIG. 18B, the view 1900 shows another actuator 1950 with a tip design that ejects gentle mist. The actuator 1950 is substantially similar to the actuator 1250 and the actuator 1850 in both external and internal structure. The actuator 1950 also includes a textured body structure 1910 and a tip 1912 that includes an upper portion 1920 and a proximate portion 822. The upper portion 1920 may have a stepped structure that limits the intrusion of the tip 1920 into nostrils.

For example, the portion 1920 may have an insert 1940 that enters a nostril and a stopping level 1932 that would contact the nostril during insertion. At the end of the upper portion 1920, there are many apertures 1916. The apertures 1916 can be a matrix of many substantially small apertures. The proximate portion 1922 connects the upper portion 1920 to the body structure 1910 and operates with the inner component 1410 to generate desired fluid pressure and volume. In some implementations, the actuator 1950 attenuates the fluid pressure even further for ejection of gentle mist of fluid.

A number of embodiments of the invention have been described. Nevertheless, it will be understood that various modifications may be made without departing from the spirit and scope of the invention. For example, instead of attenuating a fast stream of liquid into a gentle flow, a mist exiting the actuator can be transformed into a gentle cleansing stream of fluid. Accordingly, other embodiments are within the scope of the following claims.

What is claimed is:

1. A dispensing device comprising:
    a body surrounding a body cavity;
    an internal actuator; and
    a tip having a fluid path that is fluidly connected to the body cavity, wherein the internal actuator is configured to cause fluid to flow from the body cavity and to exit a distal portion of the tip along the fluid path when the internal actuator is actuated, wherein the tip includes
    a collar including an aperture positioned to surround and securely attach to the internal actuator so as to couple the tip to the internal actuator;
    one or more apertures on the distal portion of the tip, and
    an inner fluid canal that includes a stop, the stop being positioned to block fluid flow directly out of the one or more apertures when injected from the actuator and instead redirect fluid flow toward a proximate portion of the tip thereby causing fluid to pool in the canal before exiting the one or more apertures so as to reduce pressure of fluid exiting the apertures upon actuation of the internal actuator.

2. The dispensing device of claim 1, wherein the internal actuator includes a valve that is open when the internal actuator is actuated to allow the fluid flow to exit the tip.

3. The dispensing device of claim 1, wherein the internal actuator is configured to attenuate the predetermined pressure level of the fluid flow when the internal actuator is actuated.

4. The dispensing device of claim 3, wherein the internal actuator is configured to attenuate the predetermined pressure level of the fluid flow by dispensing fluid at an initial pressure but higher volume than without attenuation.

5. The dispensing device of claim 4, wherein the fluid is dispensed at the initial pressure sufficient to deliver the fluid to nasal tissue without the pressure being so great as to damage the nasal tissue.

6. The dispensing device of claim 3, wherein the internal actuator is configured to dispense the fluid as a mist when the internal actuator is actuated.

7. The dispensing device of claim 3, wherein the internal actuator is configured to attenuate the fluid flow at a plurality of different pressure levels.

8. The dispensing device of claim 7, wherein the attenuation depends on a pressure at which the internal actuator is actuated.

9. The dispensing device of claim 7, wherein at least one of the plurality of different pressure levels allows the fluid to be dispensed in large volume and low pressure with respect to a different one of the plurality of different pressure levels.

10. The dispensing device of claim 7, wherein:
    the plurality of different pressure levels include a first pressure level, a second pressure level, and a third pressure level; and
    the first pressure level is configured to attenuate the fluid flow into substantially a mist, the second pressure level is configured to attenuate the fluid flow into a stream of fluid but still faster than the mist, and the third pressure level is configured to dispense the fluid in large volume but low pressure compared to at least one of the first pressure level and the second pressure level.

11. The dispensing device of claim 1, wherein the internal actuator and the tip are formed of a same material.

12. The dispensing device of claim 1, wherein the internal actuator is integrated into the tip as a unitary structure.

13. The dispensing device of claim 1, wherein the tip includes a surface that includes the collar that surrounds and securely attaches to a portion of the body portion.

14. The dispensing device of claim 1 further including a base tube coupled with the body portion, the base tube actuated when displaced downward to open a valve for releasing pressurized fluid in the body portion.

15. The dispensing device of claim 14, wherein the tip includes a sealing portion coupled with the internal actuator to form the fluid path and configured to seal fluid from communicating from the base tube to one or more apertures in the tip.

16. The dispensing device of claim 15, wherein the sealing portion includes a stepped structure for sealing and an orifice coupled with the base tube for attenuation and regulation of fluid pressure.

17. The dispensing device of claim 16, wherein the sealing portion, the base tube, and the orifice form an integrated internal component and wherein the integrated internal component is configured to be housed inside the tip.

* * * * *